United States Patent [19]

Kempster et al.

[11] Patent Number: 5,315,243
[45] Date of Patent: May 24, 1994

[54] DETECTION AND DISCRIMINATION BETWEEN FERROMAGNETIC AND NON-FERROMAGNETIC CONDUCTIVE PARTICLES IN A FLUID

[75] Inventors: Robert W. Kempster, Ottawa; Douglas B. George, Kanata, both of Canada

[73] Assignee: Her Majesty the Queen in right of Canada, as represented by the Minister of National Defence, Ottawa, Canada

[21] Appl. No.: 866,885

[22] Filed: Apr. 6, 1992

[51] Int. Cl.$^5$ .................... G01R 33/12; G01N 27/74; G01N 33/28; G08B 21/00
[52] U.S. Cl. ...................... 324/204; 324/233; 340/641
[58] Field of Search ............... 324/204, 233, 326, 327, 324/328, 329, 225, 232; 340/631; 73/64

[56] References Cited

U.S. PATENT DOCUMENTS

| | | | |
|---|---|---|---|
| 3,665,298 | 5/1972 | Gieger | 324/239 |
| 3,748,576 | 7/1973 | Sigournay. | |
| 4,300,097 | 11/1981 | Turner | 324/233 |
| 4,651,091 | 3/1987 | Chambers et al. | |
| 4,766,373 | 8/1988 | Chambers et al. | |
| 4,926,120 | 5/1990 | Veronesi et al. | |
| 5,001,424 | 3/1991 | Kellett et al. | 324/204 |
| 5,041,856 | 8/1991 | Veronesi et al. | |

Primary Examiner—Walter E. Snow
Attorney, Agent, or Firm—Dressler, Goldsmith, Shore & Milnamow, Ltd.

[57] ABSTRACT

A device to detect the presence of particles, principally metallic particles, in fluid lines. The fluid to be sampled flows through a sensor coil which is flanked upstream and downstream by two field coils. The field coils are driven by a high frequency signal derived from a crystal oscillator and the upstream and downstream sections are wound in opposite directions such that the magnetic field from each section is cancelled out in the plane of the sense coil. When a ferromagnetic or conductive particle passes through the winding structure, the coupling in the sense coil is disturbed as the particle first interacts with the field in the upstream section of the field coil and later with the field in the downstream section of the field coil as it passes through the Sensor Coil Assembly (SCA). A characteristic signature is generated in the sense coil which results from the vector summation of these transient imbalance signals with the steady-state signal from the opposed field coils. Analysis of the phase of this signature can be used to detect and distinguish between the presence of ferromagnetic and non-ferromagnetic conductive particles. Since ferromagnetic and non-ferromagnetic conductive particles interact with the field via permeability and eddy current effects respectively, the transient phase signature has a characteristic lag-lead or lead-lag sequence depending on the nature of the particle.

12 Claims, 10 Drawing Sheets

DC BLOCK & GAIN

DETECTION AND DISCRIMINATION BETWEEN FERROMAGNETIC AND NON-FERROMAGNETIC CONDUCTIVE PARTICLES IN A FLUID

The present invention relates to a method and an apparatus for detecting the presence of particles in a fluid, particularly but not exclusively, the presence of metal particles in lubricating oil caused by wear in machinery.

BACKGROUND OF THE INVENTION

One technique for detecting on a real time basis the presence of particles in oil that has found wide acceptance is described in U.S. Pat. No. 4,651,091, inventors Chambers and Waggoner, issued Mar. 17, 1987.

However, the technique described in that patent cannot discriminate between ferromagnetic and non-ferromagnetic particles.

SUMMARY OF THE INVENTION

The present invention seeks to provide a novel real-time technique for detecting the presence of particles in a fluid which lends itself to discriminating easily between ferromagnetic particles and non-ferromagnetic conductive particles.

The method generally involves establishing a balanced A.C. magnetic field at a region of the fluid stream and then detecting any disturbances in the balanced field caused by particles in the fluid stream passing through the region. The use of a balanced field tends to eliminate or reduce spurious signals arising from temperature variations or the like because both fields which contribute to the balanced field are equally and oppositely affected.

In addition, ferromagnetic particles give rise to a first unique disturbance characteristic or signature which can be described simply as a signal portion of one phase followed by a signal portion 180° out of phase and non-ferromagnetic conductive particles have a second unique disturbance signature which is a mirror image of the first characteristic. This enables ferromagnetic particles such as steel to be distinguished from non-ferromagnetic conductive particles such as aluminum or copper simply by analyzing the disturbance.

DETAILED DESCRIPTION OF A PREFERRED EMBODIMENT

Figure 1:
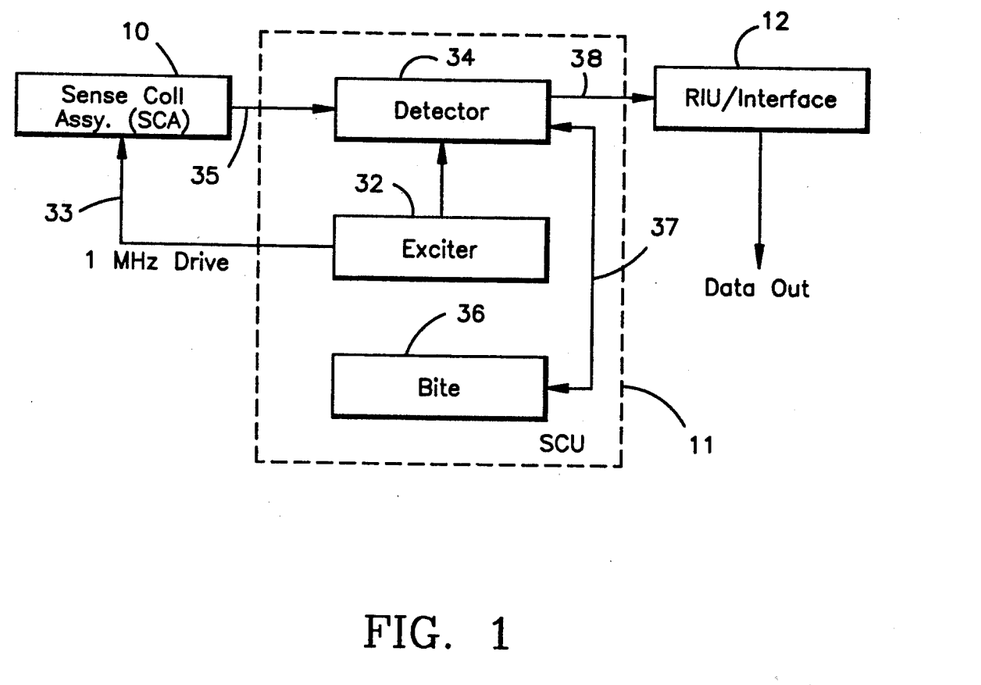
FIG. 1 is a functional block diagram of a particle detector according to the invention.
Figure 2:
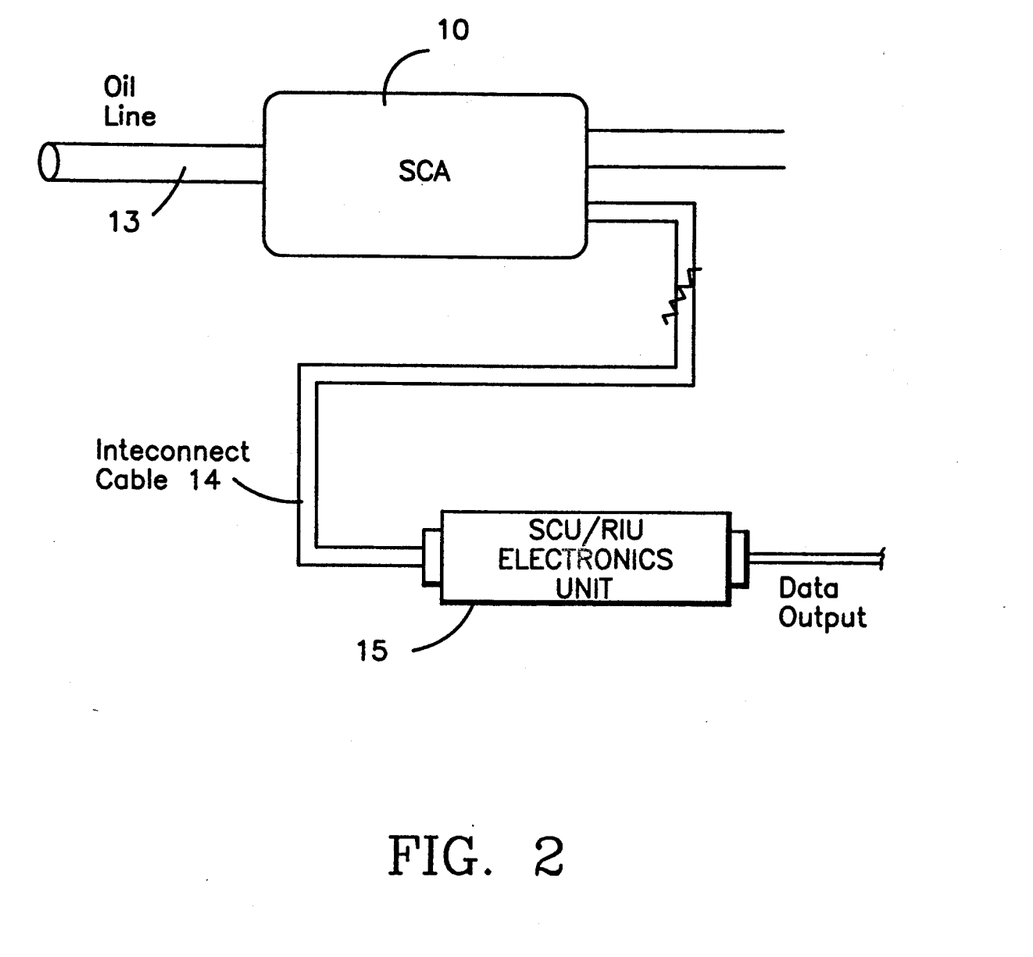
FIG. 2 illustrates the mechanical configuration of the particle detector of FIG. 1.

With reference to FIG. 1, the particle detector of the invention comprises a sense coil assembly (SCA) 10, a signal conditioning unit (SCU) 11 and a readout interface unit (RIU) 12. As shown in FIG. 2, the SCA 10 in use is mounted on an oil pipe 13 and is interconnected by means of a cable 14 to the SCU 11 and RIU 12 which are packaged together at a remote location in an electronics unit 15.

Figure 3:
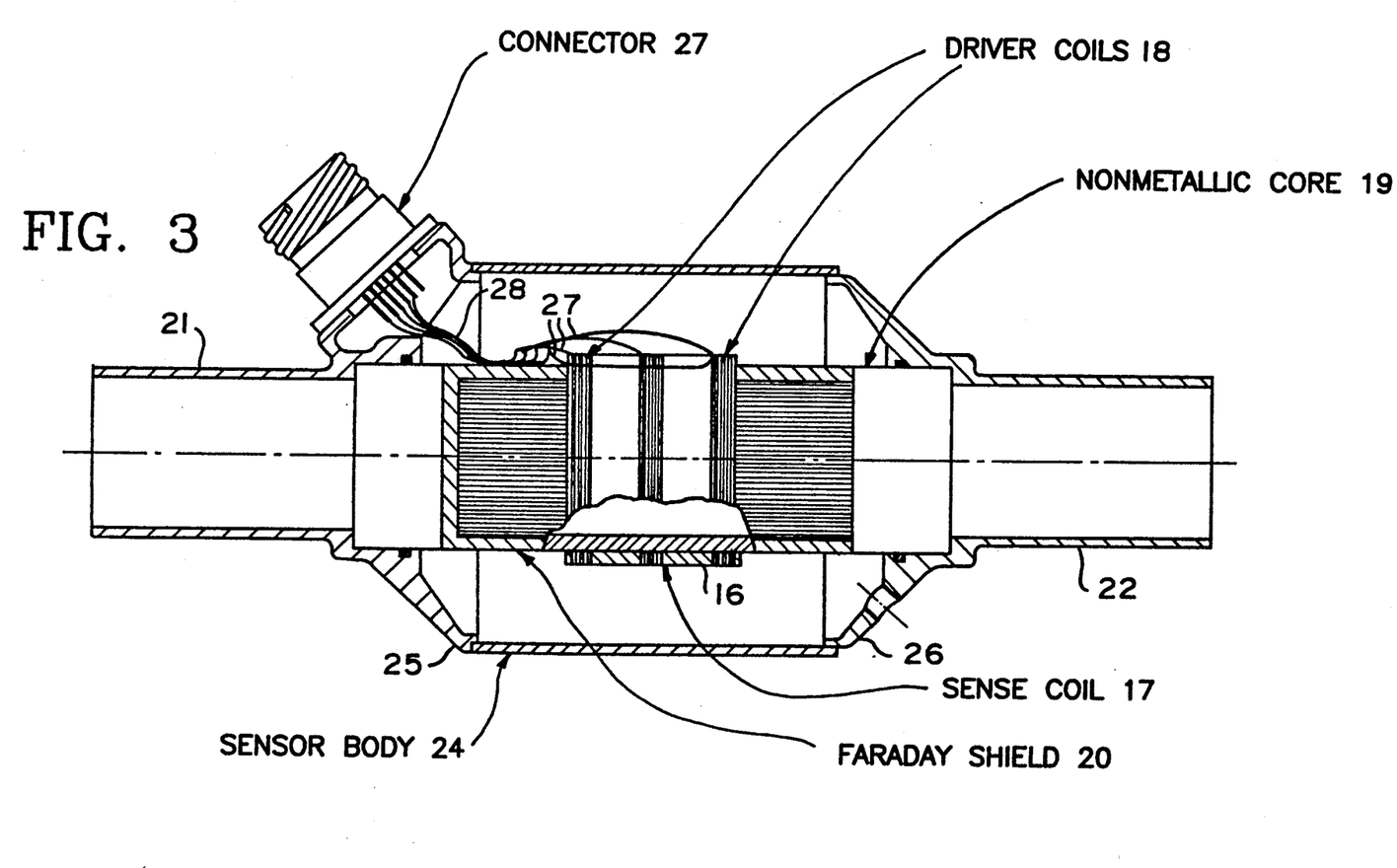
FIG. 3 is a longitudinal sectional view of a sensor coil assembly, which forms part of the particle detector, shown in situ.

Referring now to FIG. 3, the SCA 10 comprises a bobbin 16 on which are wound a copper sense coil 17 located equidistantly from upstream and downstream field or drive coils 18, the two field coils being wound in opposite senses from each other. The bobbin is carried on a non-metallic cylindrical core or former 19 which may be made of a high-temperature-resistant sintered plastic material such as TORLON. The bobbin may also be made of TORLON or ceramic, with a Faraday shield 20 sandwiched between the bobbin and the core 19. A layer of insulation may be applied over the Faraday shield.

The non-metallic core 19 is coupled at each end to a pipe section 21 and 22 which is adapted to be connected into the oil line 13 (FIG. 2). A cylindrical sensor body 24 extends between widened diameter portions 25 and 26 of pipe sections 21 and 22 such that sensor body 24 is generally concentric with and surrounds core 19 in spaced relation thereto. Body 24 serves to provide physical protection for the coils and other components of the SCA and to provide shielding from external electromagnetic fields and typically is made from aluminum. Leads 27 from the coils are gathered together into a harness 28 which is adapted to be connected to the cable 14 via a connector 29.

Referring again to FIG. 1, the SCU 11 comprises three blocks, namely an exciter 32 connected to drive the SCA via a line 33, a signal detector 34 connected to an output 35 of SCA 10 and built-in test equipment (BITE) circuits 36 connected to detector 34 via line 37 for inserting and detecting a test signal to verify operation of the entire sensing system. An output 38 of detector 34 is connected to an input of RIU 12.

In operation, with clean (i.e. lacking metallic particles) oil flowing through oil line 13 and a 1 MHz drive signal being fed from exciter 32 to the field coils 18, there is essentially no output signal from the sense coil 17 since the field coils are wound in opposite directions thereby causing two magnetic fields generated in the plane of the sense coil by the field coils to be substantially balanced and cancelled out.

However, when a ferromagnetic particle present in the oil passes into the region of the upstream field coil, it increases the magnetic coupling between the upstream field coil and the sense coil and later, as it passes into the region of the downstream field coil, it increases the magnetic coupling between the downstream field coil and the sense coil. When a non-ferromagnetic conductive particle present in the oil passes into the region of the upstream field coil, it decreases the magnetic coupling between the upstream field coil and the sense coil and later, as it passes into the region of the downstream field coil, it decreases the magnetic coupling between the downstream field coil and the sense coil. These phenomena give rise to a varying signal derived from the sense coil which is detected and processed in detector 34 and the output of the detector is then used to give a readout via RIU 12 of data relating to the particle.

The sensing and processing of the sensed signal will be described in detail hereinbelow. Suffice it to say, for the time being, that the sense coil produces a characteristic output which signifies whether the particle is ferromagnetic or non-ferromagnetic and indicates the size of the particle.

Figure 4:
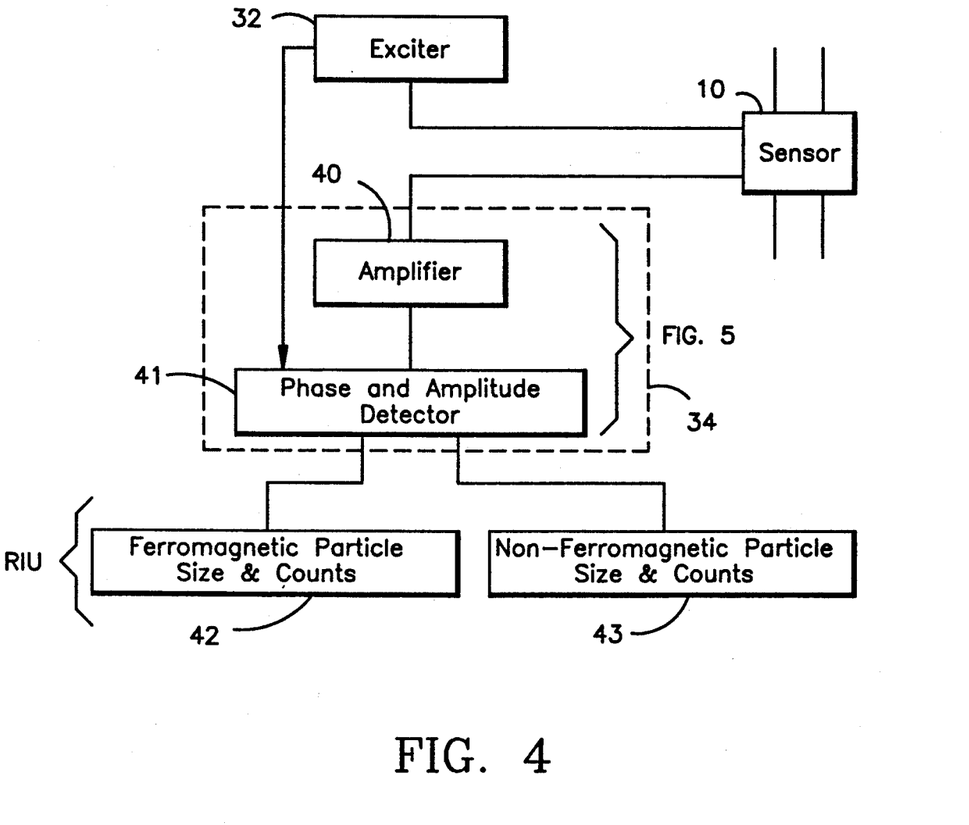
FIG. 4 is a more detailed block diagram of the detector illustrated in FIG. 1.

FIG. 4 is a slightly more detailed version of FIG. 1 and shows detector 34 as comprising an amplifier block 40 feeding a phase and amplitude detector 41. The RIU 12 of FIG. 1 is shown in FIG. 4 as two blocks 42 and 43 for counting and indicating size of ferromagnetic particles and non-ferromagnetic particles, respectively.

Figure 5:
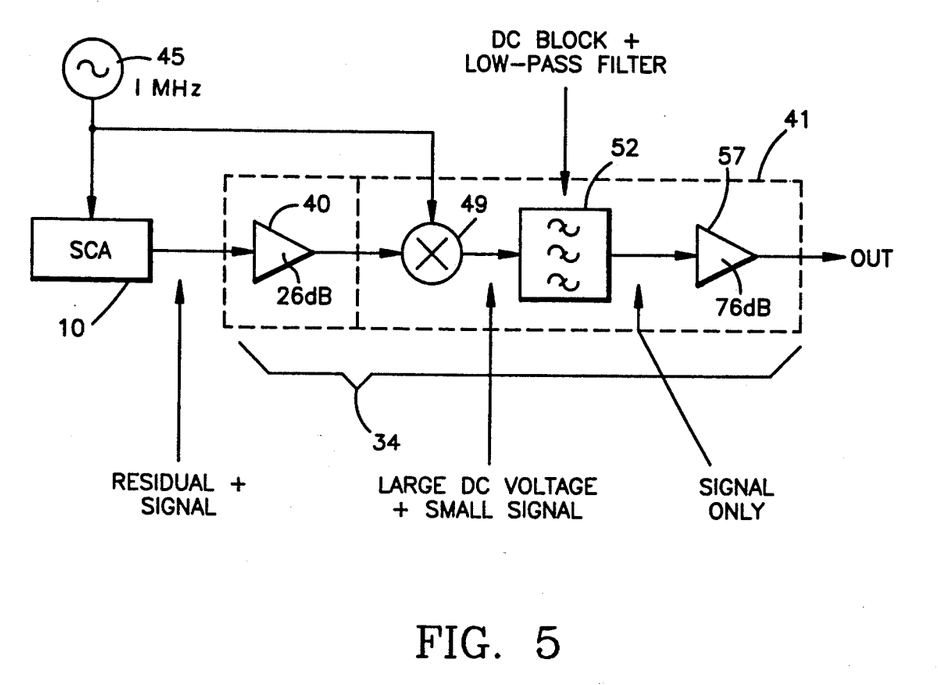
FIG. 5 is a block diagram illustrating in greater detail the components of FIG. 4.
Figures 6A, 6B:
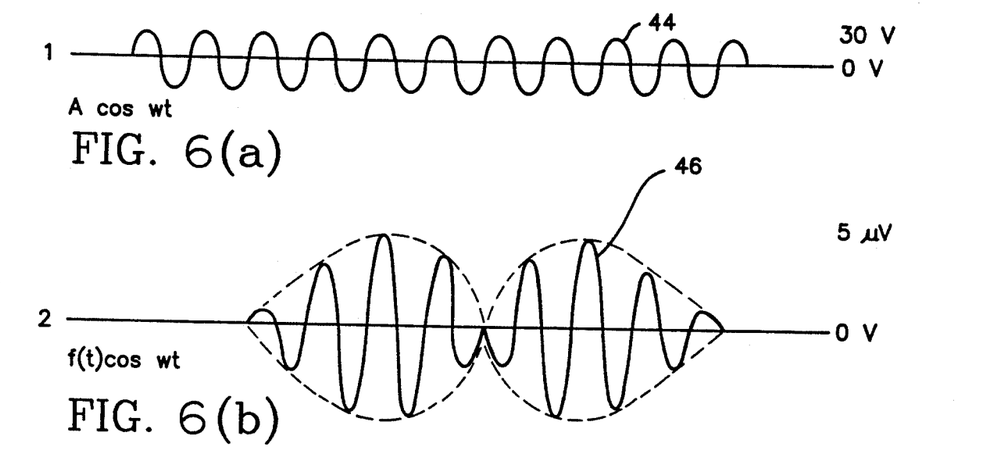
FIGS. 6(a)–6(d) are diagrams illustrating waveforms present at different points in FIG. 5.

Reference should now be made to FIG. 5 in conjunction with FIGS. 6 and 7 for a more detailed operation of the invention. A 30 volt 1 MHz drive signal 44 shown at FIG. 6(a) is applied to SCA 10 from the exciter 32, shown schematically in FIG. 5 as an oscillator 45 which, in fact, forms only part of the exciter. If a ferromagnetic particle is present in the oil flowing through the particle detector, a characteristic signal 46 shown in FIG. 6(b) is generated by the sense coil 17. It can be seen that signal 46 has the same frequency as the drive signal 44 and is initially in phase with drive signal 44, the amplitude steadily increasing and then decreasing in value as the particle moves between the upstream field coil 18 and the sense coil 17. As the particle moves between the sense coil 17 and the downstream field coil 18 again the amplitude rises from zero through the maximum and back to zero but now the signal 46 is 180° out of phase with respect to signal 44.

Figure 6C:
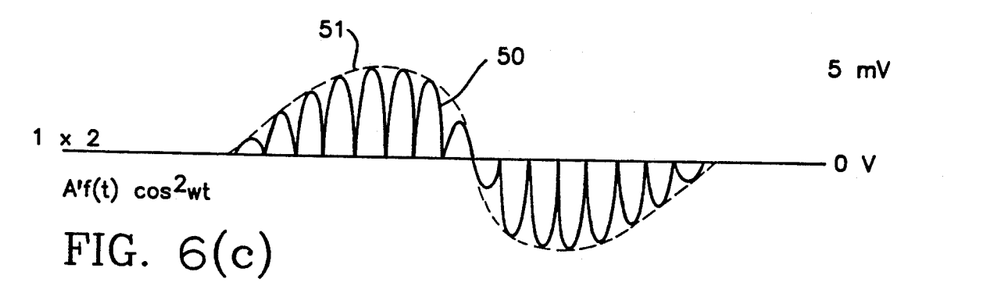

Signal 46 is fed from SCA 10 through amplifier 40 to a mixer 49 where it is mixed with a 1 MHz signal from the oscillator 45 to derive a signal 50 illustrated in FIG. 6(c). It can be seen that the envelope 51 of signal 50 is a sine wave which follows the positive envelope of signal 46 over the portion that signal 46 is in-phase with signal 44 and then follows the negative envelope of signal 46 over that portion of signal 46 where it is out of phase with signal 44.

Figure 6D:
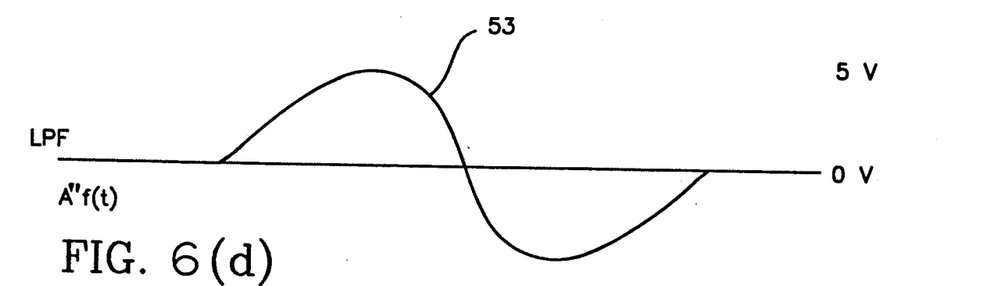
Figure 7A:
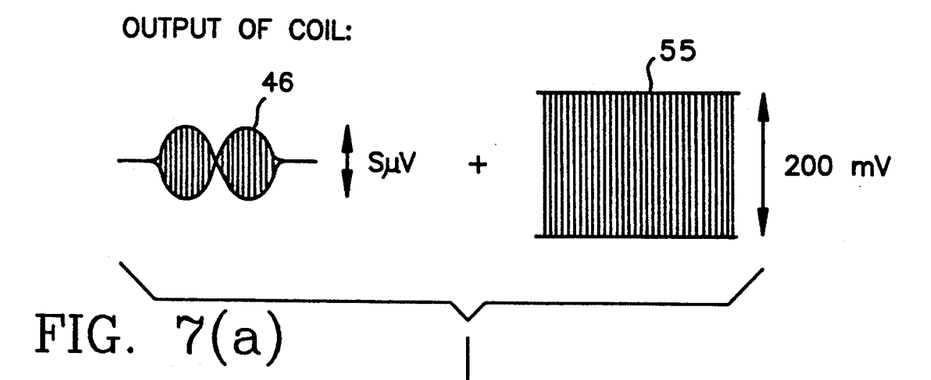
FIGS. 7(a)–7(c) are diagrams illustrating the function of a filter of FIG. 5.

Signal 50 is then passed through a low-pass filter 52 and amplified to obtain a signal 53, shown in FIG. 6(d), which is a sine wave following the envelope 51 of signal 50. Actually filter 52 is also constructed as a D.C. blocking filter as well as a low-pass filter for the following reason. If the field coils 18 are spaced exactly the same distance from the sense coil 17 and are wound accurately, in theory the two fields generated in the plane of the sense coil 17 should cancel. In practice, however, there is always some minor discrepancy and this gives rise to the derivation of a residual signal 55, which typically should be no larger than 200 mV, which is shown in FIG. 7(a) along with signal 46 which is the signal caused by the presence of a moving ferromagnetic particle.

Figure 7B:
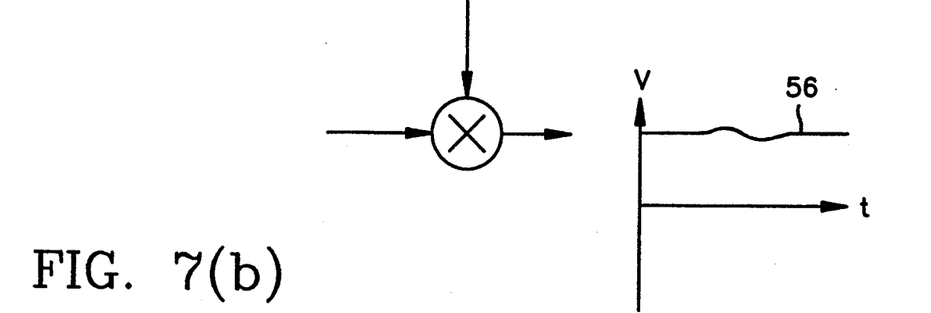
Figure 7C:
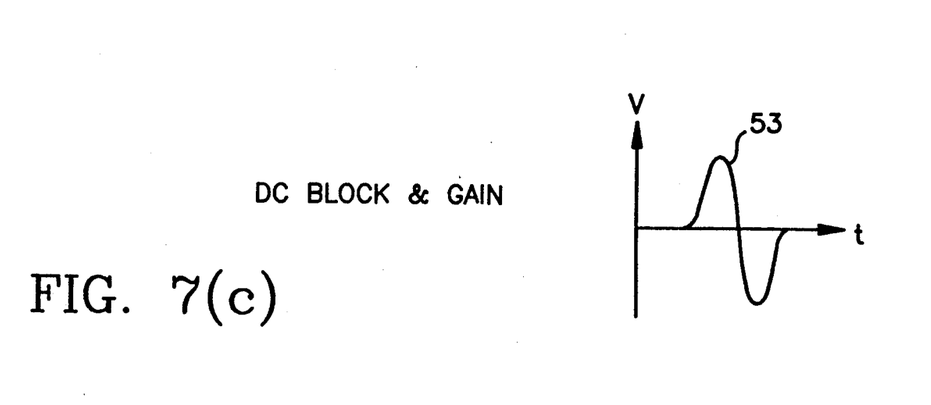

The output of mixer 49 is shown in FIG. 7(b) and this can be seen to be a D.C. component 56 on which is superimposed the signal 50 of FIG. 6(c). After passage through filter 52 the D.C. component 56 has been removed and the envelope 51 reproduced and after amplification by amplifier 57 the signal 53 shown in FIGS. 6(d) and 7(c) is obtained.

It is noted that the signal 53 indicates by its magnitude the size of the ferromagnetic particle detected. The duration of the signal simply indicates the speed at which the particle passed through the SCA 10, typically between 1 and 3 msecs. More importantly, the phase of signal 53 indicates whether the particle detected is ferromagnetic or non-ferromagnetic. This can be explained as follows. If a non-ferromagnetic particle, aluminum for example, had been detected, the sensed signal 46 would have comprised a first portion out of phase with drive signal 44 and a second portion in-phase with signal 44, i.e., exactly the opposite of signal 46 illustrated in FIG. 6(b). The reason for the difference is that non-ferromagnetic particles interact with the field via eddy currents rather than permeability in the case of ferromagnetic particles. The end result is that, in the case of a non-ferromagnetic particle, signal 53 would be the mirror image of signal 53 shown in FIG. 6(d) i.e., the first half of the signal would be negative and the second half positive.

Signal 53 can easily be processed by known techniques for example by means of threshold detectors to sample signal 53 and drive counters to indicate whether ferromagnetic or non-ferromagnetic and to indicate also the size of the particle. More particularly, if a negative threshold detector is tripped within a predetermined time after a positive threshold detector has been tripped, this indicates a positive signal half followed by a negative signal half as illustrated in FIG. 7(c), thereby signalling a ferromagnetic particle. If, on the other hand, the positive threshold detector is tripped after the negative threshold detector, this indicates a mirror image of the signal 53 shown in FIG. 7(c), thereby signalling a non-ferromagnetic particle. These functions as well as counting the actual number of particles sensed are generally referred to by blocks 42 and 43 in FIG. 4.

A potential problem arises from the presence of air or water bubbles in the oil which give rise to interaction with electric fields causing spurious signals or noise to be detected in the sense coil 17. The Faraday shield 20 is located between the coils and the fluid, effectively blocking electric fields and avoiding spurious signals resulting from the presence of air bubbles.

Figure 8:
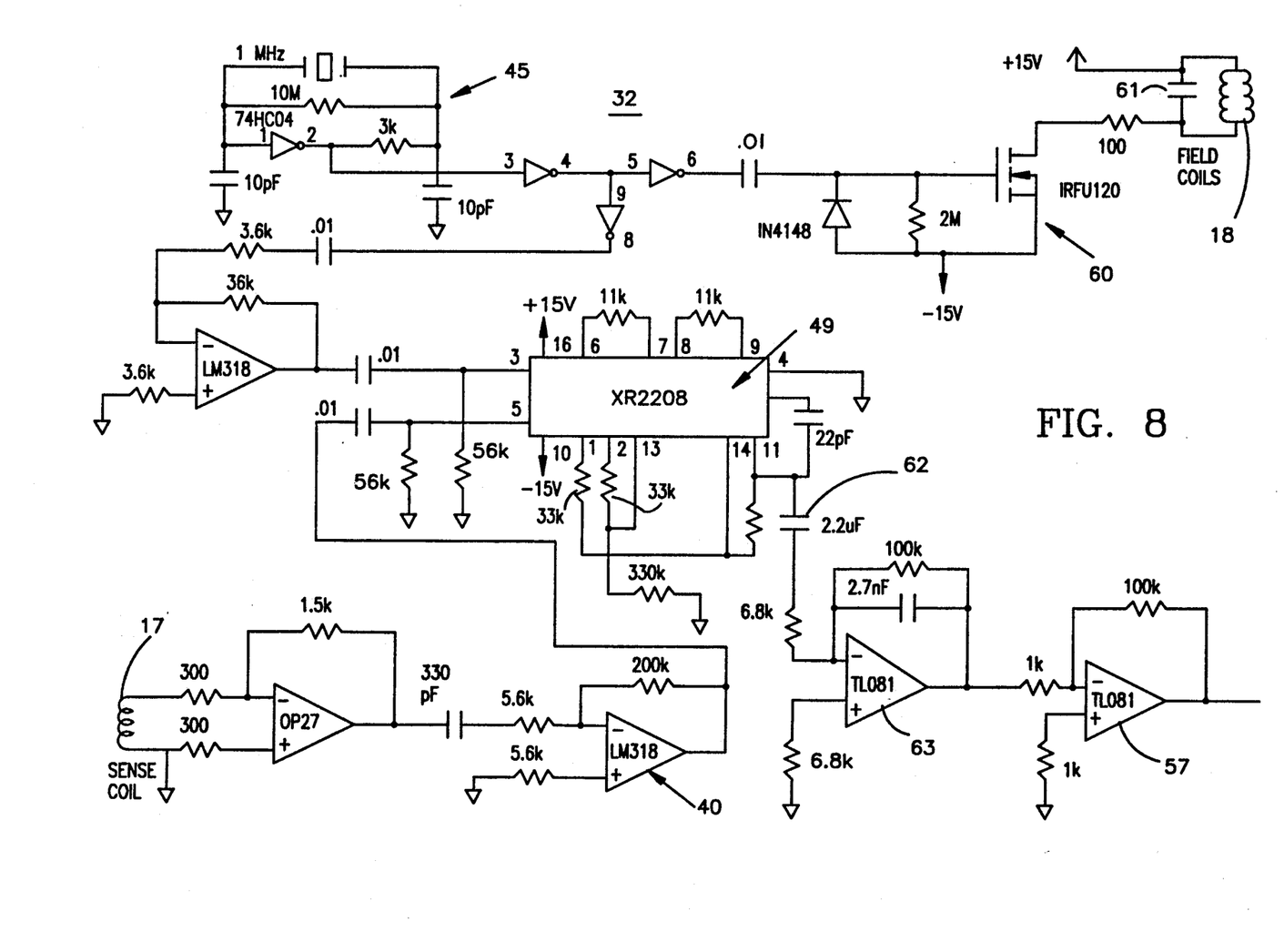
FIG. 8 is a schematic diagram illustrating the components of FIG. 5 in greater detail.

FIG. 8 illustrates the circuit components of the block diagram of FIG. 5. The oscillator 45 comprises a 1 MHz crystal combined in known fashion with resistors, capacitors and inverters. In addition to oscillator 45 the exciter 32 comprises a driver 60 consisting of an FET, resistor and diode as well as a capacitor 61 which is connected across the field coils 18 and forms therewith a resonant circuit. The use of the tuned circuit enhances the field energy provided.

Mixer 49 of FIG. 5 is in the form of an XR2208 multiplier chip having an input pin number 3 connected to oscillator 45 and an input pin number 5 connected to amplifier 40. The mixed output is at pin number 11 and a capacitor 62 serves as the D.C. blocking portion of filter 52 in FIG. 5. The low-pass filter portion of filter 52 is formed of op.amp circuit 63.

It should be noted that the result of the multiplication in the multiplier chip is an output consisting of sum and difference frequencies and harmonics. All of these signal components are in the radio frequency range with the exception of the difference frequency between the 1 MHz reference signal 44 and the sense coil signal 46 (FIG. 6). Since the frequency of these signals is identical, the "difference frequency" output of the multiplier in the absence of a particle target is the D.C. voltage 56 (FIG. 7). When a particle target is present, a characteristic low frequency signature is superimposed on the D.C. voltage 56 as shown in FIG. 7(b). Because all other multiplier outputs are of much higher frequency than particle signatures they can be eliminated by integration in the post-detection amplifier 63 (FIG. 8), leaving only the relevant low-frequency signals. Note that this principle also eliminates almost all interfering R.F. signals and harmonics of the 1 MHz field drive.

Figure 10:
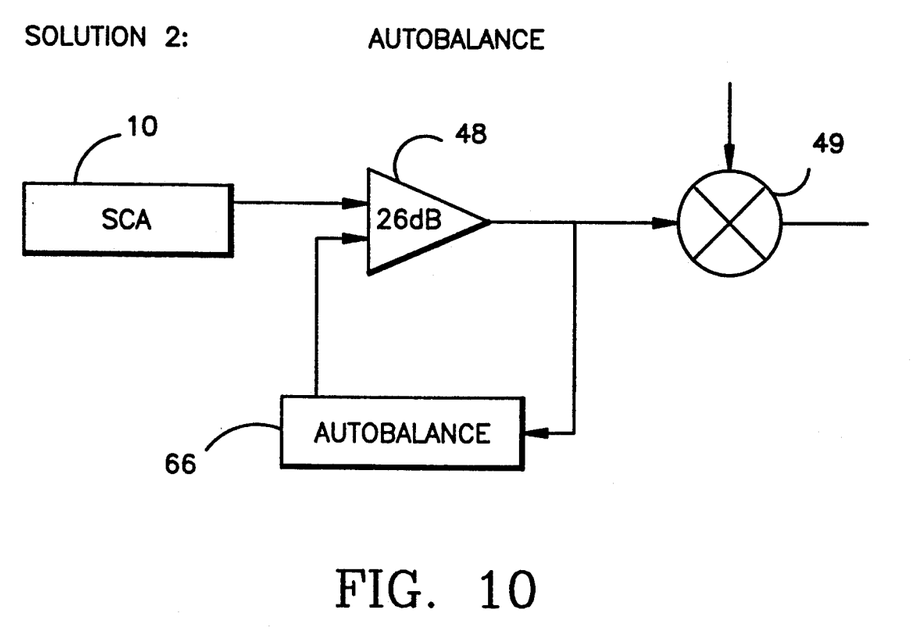
FIG. 10 is a block diagram illustrating an autobalance feature.

The multiplier chip functions on a few mV of signal and so the demand for gain at signal frequency is minimized thus easing design problems with stability. This detector design also reduces balance requirements in the SCA 10 since the main requirement for balance is now dictated by the need to avoid overdriving and saturation of the sense coil signal amplifiers, a condition relatively easy to meet as gain requirements are modest. Although, in principle, the design will operate satisfactorily without any balance provision, if the SCA 10 cannot be manufactured to a sufficiently high tolerance the residual signal 55 may become unacceptably high in which case an automatic balancing (autobalance) circuit may be necessary. FIG. 10 illustrates generally the principle in which an autobalance block 66 is positioned to feed back the output of differential amplifier 40 to an input of differential amplifier 40 in opposition to the signal supplied by SCA 10. The autobalance block 66 feeds back the signal which is obtained when no particle is present to subtract from the signal which is obtained when a particle is present thereby cancelling the residual.

Figure 9:
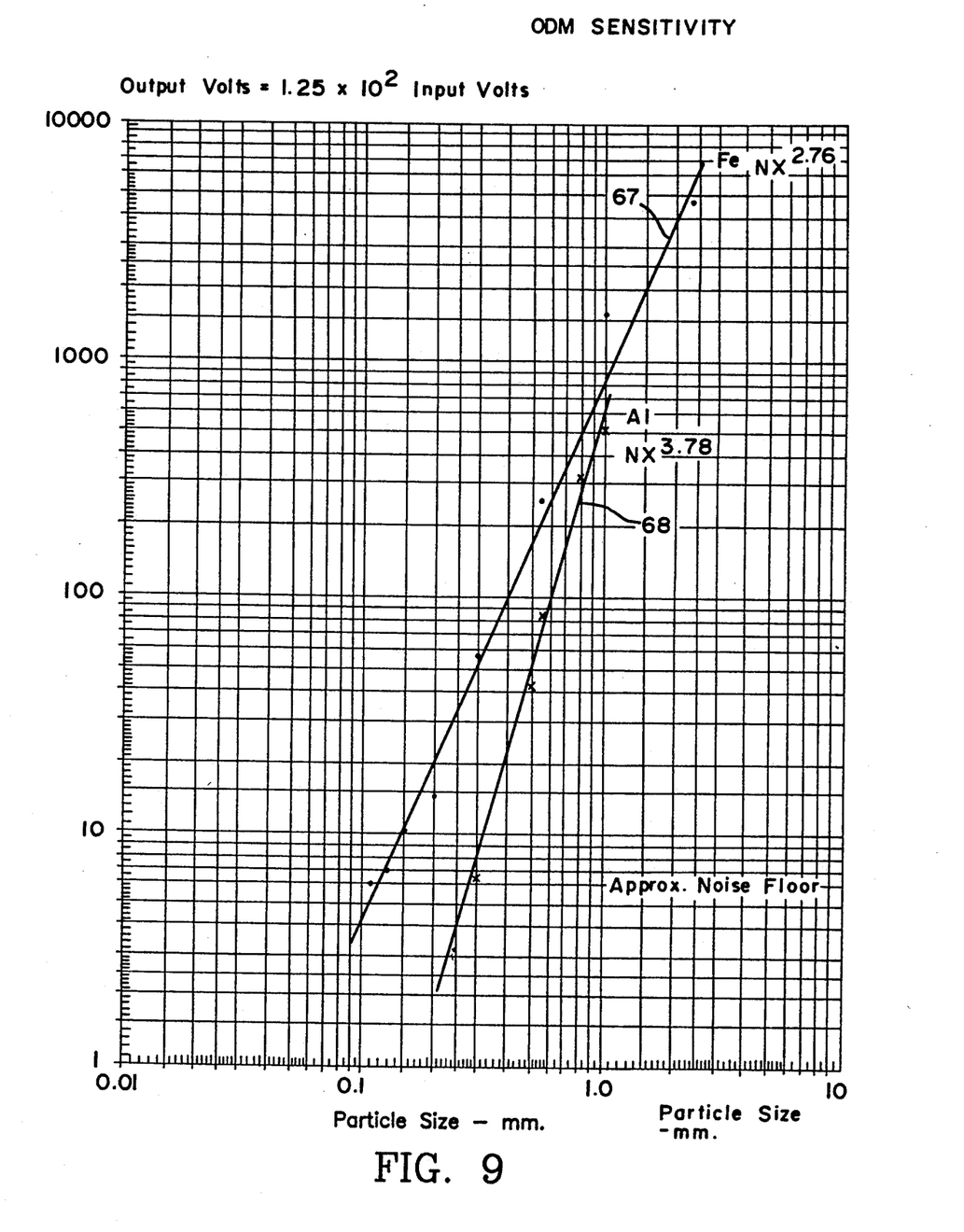
FIG. 9 is a graph illustrating the response of the detector versus particle size for ferrous and aluminum particles.

FIG. 9 shows the relationship found between particle size and signal-to-noise ratio of the sensed signal. Line 67 shows the results for ferrous particles and line 68 for aluminum particles.

Using the present invention spherical ferromagnetic particles of 125 microns or larger in diameter or spherical aluminum particles of about 250 microns or larger in diameter can be detected with high probability.

In addition to the expected ferromagnetic and non-ferromagnetic signature sequences, another phenomenon has been noted. Typically, if the sequence of amplitude and phase changes which constitute a target signature are displayed on a double-beam oscilloscope together with a reference trace derived from the field drive, the normally observed sequence as the target particle traverse the detection region is a growing in-phase signature which reaches a maximum then reverses rapidly to an antiphase condition before fading back to the steady state residual of the sense coil winding (which may display any phase), or the reverse of this sequence, depending on ferromagnetic or non-ferromagnetic nature of the target. A class of targets was found, however, in which a marked excursion in phase of the signature was noted both before and after the central rapid axis-crossing of the aperture. This class of targets is identified tentatively as those of a material which is mildly magnetic and also conductive, thus leading to an interaction between non-ferromagnetic and ferromagnetic responses. Perhaps significantly, non-conducting ferrite targets (having only magnetic properties) always display the expected in-phase/anti-phase sequence.

Although the present invention is primarily intended for use in discriminating between ferromagnetic and non-ferromagnetic particles and determining the size of the particles, the technique might also yield the measurement of other properties or characteristics. If particles of the same size are detected, copper could be discriminated from aluminum.

In the above description of the invention, the expression "particle size". For non-spherical ferromagnetic particles, the same signature is produced by a particle having the same volume (mass). For non-spherical conductive particles, the same signature is produced by a particle having the same largest conductive loop area.

We claim:

1. Apparatus for detecting the presence of solid ferromagnetic particles or solid non-ferromagnetic conductive particles entrained in a stream of fluid comprising three coaxial coils arranged to encompass the stream, one of the coils being a sense coil and the other coils being field coils located respectively upstream and downstream with reference to the sense coil, one field coil being wound in a first direction and the other field coil being wound in the opposite direction, means for energizing the field coils to generate A.C. magnetic fields and establish opposing A.C. magnetic fields at the sense coil, means connected to the sense coil to detect a disturbance of the A.C. magnetic field present at the sense coil when a particle moves through the coils and to provide a signature electrical signal indicative of a disturbance, means for removing any residual electrical signal due to imbalance of the opposing A.C. magnetic fields from that signature electrical signal and provide an output signal and means to analyze the phase of the output signal so as to discriminate between ferromagnetic and non-ferromagnetic conductive particles, wherein the means for removing any residual electrical signal is a differential amplifier having one input supplied with an output from the sense coil, an output of the differential amplifier being connected to an input of an autobalance circuit whose output is connected to another input of the differential amplifier, the output of the differential amplifier being connected to a mixer whose other input is supplied with a signal of the same frequency as the A.C. magnetic fields, the mixer's output providing said output signal.

2. Apparatus according to claim 1 in which the field coils are substantially equidistant from the sense coil and the field generated by each field coil is substantially identical and at the same frequency and phase whereby the fields are substantially cancelled at the sense coil when no particle is present.

3. Apparatus according to claim 2 including means to analyze the magnitude of the disturbance so as to determine particle size.

4. Apparatus for detecting the presence of solid ferromagnetic particles or solid-ferromagnetic conductive particles entrained in a stream of fluid comprising three coaxial coils arranged to encompass the stream, one of the coils being a sense coil and the other coils being field coils located respectively upstream and downstream with reference to the sense coil, one field coil being wound in a first direction and the other field coil being wound in the opposite direction with both field coils being connected to an oscillator that provides a signal whereby the field coils generate opposing A.C. magnetic fields of the same frequency and establish a balanced A.C. magnetic field at a region of the stream surrounded by the sense coil which can detect, by an inductively generated signal, any disturbance of the balanced A.C. magnetic field created by a particle moving in the stream through the region; an output of the sense coil being connected to a mixer having another input connected to said oscillator to generate a difference signal at the mixer's output indicative of any disturbance of the balanced A.C. magnetic field, the difference signal being applied to a low pass filter with D. C. blocking which provides an output signal to a phase detector and analyzer that determines the phase of the output signal of discriminate between ferromagnetic and non-magnetic particles.

5. Apparatus according to claim 4 in which the field coils are connected in parallel to each other and a capacitor forming a resonant circuit having a resonant frequency equal to the frequency of the oscillator's signal.

6. Apparatus according to claim 5 in which the phase detector and analyzer includes threshold detectors to sample the filter's output signal, the threshold detectors driving counters to indicate the number of ferromagnetic or non-ferromagnetic particles detected.

7. Apparatus according to claim 6 in which the phase detector and analyzer determines the magnitude of any disturbance to determine the size of a particle which created the disturbance.

8. Apparatus according to claim 7 in which a Faraday shield is located between the three coaxial coils and the stream.

9. A method of detecting the presence of solid ferromagnetic particles or solid non-ferromagnetic conductive particles entrained in a stream of fluid comprising establishing a balanced A.C. magnetic field at a region of the stream by generating a first A.C. magnetic field at an upstream location with respect to said region and simultaneously generating an opposing A.C. magnetic field at the same frequency at a downstream location with respect to said region and detecting a disturbance of the balanced A.C. magnetic field caused by a particle moving in the stream through said region by inductively generating an electrical signal from the A.C. magnetic field at said region, then mixing the electrical signal with a reference electrical signal at the same frequency thereby generating a difference frequency and removing any residual electrical signal due to imbalance of the opposing A.C. magnetic fields to provide an output signal, then analyzing the phase of the output signal at different portions to discriminate between ferromagnetic and non-ferromagnetic particles.

10. A method according to claim 9 in which the upstream and downstream locations are substantially equidistant from the region and the first and opposing A.C. magnetic fields are substantially equal to each other.

11. A method according to claim 10 comprising analyzing the amplitude of the electrical signal to determine the size of a particle.

12. A method according to claim 9 in which the phase analyzing step comprises differentiating between a first shape of output signal and a mirror image shape in order to discriminate between a ferromagnetic and a non-ferromagnetic particle.

* * * * *

UNITED STATES PATENT AND TRADEMARK OFFICE
CERTIFICATE OF CORRECTION

PATENT NO. : 5,315,243
DATED : May 24, 1994
INVENTOR(S) : Robert William Kempster et al.

It is certified that error appears in the above-identified patent and that said Letters Patent is hereby corrected as shown below:

Column 5, line 31, "signal-to-noise ratio" should read: --amplitude--.

Column 6, line 49 (claim 4, line 2), "solid-ferromagnetic" should read: --solid non-ferromagnetic--.

Column 7, line 4 (claim 4, line 25), after "output signal", "of" should read: --to--.

Signed and Sealed this

Twentieth Day of September, 1994

Attest:

BRUCE LEHMAN

Attesting Officer

Commissioner of Patents and Trademarks